United States Patent
Kroon et al.

(10) Patent No.: US 10,531,906 B2
(45) Date of Patent: Jan. 14, 2020

(54) MEDICAL VAPOR GENERATOR

(71) Applicant: Uptake Medical Technology Inc., Seattle, WA (US)

(72) Inventors: Joshua Pieter Kroon, Seattle, WA (US); Erik Henne, Seattle, WA (US); Daniel Lawrence Reddy, Seattle, WA (US); Robert Alan Mest, Long Beach, CA (US); Ryan Welty, Blaine, MN (US)

(73) Assignee: Uptake Medical Technology Inc., Seattle, WA (US)

( * ) Notice: Subject to any disclaimer, the term of this patent is extended or adjusted under 35 U.S.C. 154(b) by 467 days.

(21) Appl. No.: 15/013,748

(22) Filed: Feb. 2, 2016

(65) Prior Publication Data
US 2016/0220297 A1  Aug. 4, 2016

Related U.S. Application Data

(60) Provisional application No. 62/111,033, filed on Feb. 2, 2015, provisional application No. 62/153,352, filed on Apr. 27, 2015.

(51) Int. Cl.
*A61B 18/04* (2006.01)
*A61B 18/00* (2006.01)

(52) U.S. Cl.
CPC .... *A61B 18/04* (2013.01); *A61B 2018/00541* (2013.01); *A61B 2018/00744* (2013.01);
(Continued)

(58) Field of Classification Search
CPC .......... A61B 18/04; A61B 2018/00541; A61B 2018/00744; A61B 2018/00791; A61B 2018/048; A61M 5/002; A61M 5/1452
See application file for complete search history.

(56) References Cited

U.S. PATENT DOCUMENTS

| 408,899 A | 8/1889 | Small |
| 1,719,750 A | 7/1929 | Bridge et al. |

(Continued)

FOREIGN PATENT DOCUMENTS

| AU | 721086 B2 | 6/2000 |
| EP | 1003582 B1 | 2/2003 |

(Continued)

OTHER PUBLICATIONS

Becker, et al.; Lung volumes before and after lung volume reduction surgery; Am J Respir Crit Care Med; vol. 157; pp. 1593-1599; (1998) Oct. 28, 1997.

(Continued)

*Primary Examiner* — Michael F Peffley
*Assistant Examiner* — Khadijeh A Vahdat
(74) *Attorney, Agent, or Firm* — Richard Batt

(57) ABSTRACT

A medical vapor system and method is provided. The medical vapor system can include a fluid conduit having an inlet, an outlet and a heating section, the inlet being adapted and configured to be connected to a source of liquid water, a resistance heater disposed and configured to generate heat and conduct the heat to the heating section of the fluid conduit to vaporize liquid water flowing through the heating section, a power supply operatively connected to the heater, and a controller adapted to control production of water vapor by the system. Methods of use are also provided.

20 Claims, 3 Drawing Sheets

(52) U.S. Cl.
CPC ............... *A61B 2018/00791* (2013.01); *A61B 2018/048* (2013.01)

(56) References Cited

U.S. PATENT DOCUMENTS

| | | | |
|---|---|---|---|
| 3,507,283 A * | 4/1970 | Thomas, Jr. .......... | A61B 18/02 606/24 |
| 3,880,168 A | 4/1975 | Berman | |
| 4,026,285 A | 5/1977 | Jackson | |
| 4,713,060 A * | 12/1987 | Riuli .................... | A61M 5/002 604/199 |
| 4,773,410 A | 9/1988 | Blackmer et al. | |
| 4,793,352 A | 12/1988 | Eichenlaub | |
| 4,915,113 A | 4/1990 | Holman | |
| 4,950,266 A | 8/1990 | Sinofsky | |
| 5,006,119 A | 4/1991 | Acker et al. | |
| 5,011,566 A | 4/1991 | Hoffman | |
| 5,084,043 A | 1/1992 | Hertzmann et al. | |
| 5,112,328 A | 5/1992 | Taboada et al. | |
| 5,158,536 A | 10/1992 | Sekins et al. | |
| 5,263,951 A | 11/1993 | Spears et al. | |
| 5,331,947 A | 7/1994 | Shturman | |
| 5,334,190 A | 8/1994 | Seiler | |
| 5,348,551 A | 9/1994 | Spears et al. | |
| 5,352,512 A | 10/1994 | Hoffman | |
| 5,424,620 A | 6/1995 | Cheon et al. | |
| 5,425,414 A | 6/1995 | Bradley, Jr. et al. | |
| 5,462,521 A | 10/1995 | Brucker et al. | |
| 5,500,012 A | 3/1996 | Brucker et al. | |
| 5,503,638 A | 4/1996 | Cooper et al. | |
| 5,524,620 A | 6/1996 | Rosenschein | |
| 5,529,076 A | 6/1996 | Schachar | |
| 5,549,628 A | 8/1996 | Cooper et al. | |
| 5,562,608 A | 10/1996 | Sekins et al. | |
| 5,575,803 A | 11/1996 | Cooper et al. | |
| 5,591,157 A | 1/1997 | Hennings et al. | |
| 5,620,440 A | 4/1997 | Heckele et al. | |
| 5,695,507 A | 12/1997 | Auth et al. | |
| 5,735,811 A | 4/1998 | Brisken | |
| 5,752,965 A | 5/1998 | Francis et al. | |
| 5,755,753 A | 5/1998 | Knowlton | |
| 5,782,914 A | 7/1998 | Schankereli | |
| 5,800,482 A | 9/1998 | Pomeranz et al. | |
| 5,824,703 A | 10/1998 | Clark, Jr. | |
| 5,827,268 A | 10/1998 | Laufer | |
| 5,913,856 A | 6/1999 | Chia et al. | |
| 5,957,919 A | 9/1999 | Laufer | |
| 5,964,752 A | 10/1999 | Stone | |
| 5,972,026 A | 10/1999 | Laufer et al. | |
| 5,986,662 A | 11/1999 | Argiro et al. | |
| 5,989,445 A | 11/1999 | Wise et al. | |
| 6,032,077 A | 2/2000 | Pomeranz | |
| 6,053,909 A | 4/2000 | Shadduck | |
| 6,059,011 A | 5/2000 | Giolo | |
| 6,083,255 A | 7/2000 | Laufer et al. | |
| 6,099,251 A | 8/2000 | LaFleur | |
| 6,102,037 A | 8/2000 | Koch | |
| 6,113,722 A | 9/2000 | Hoffman et al. | |
| 6,130,671 A | 10/2000 | Argiro | |
| 6,131,570 A | 10/2000 | Schuster et al. | |
| 6,139,571 A | 10/2000 | Fuller et al. | |
| 6,156,036 A | 12/2000 | Sussman et al. | |
| 6,162,232 A | 12/2000 | Shadduck | |
| 6,179,805 B1 | 1/2001 | Sussman et al. | |
| 6,194,066 B1 | 2/2001 | Hoffman | |
| 6,200,333 B1 | 3/2001 | Laufer | |
| 6,210,404 B1 | 4/2001 | Shadduck | |
| 6,219,059 B1 | 4/2001 | Argiro | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,299,633 B1 | 10/2001 | Laufer | |
| 6,300,150 B1 | 10/2001 | Venkatasubramanian | |
| 6,312,474 B1 | 11/2001 | Francis et al. | |
| 6,327,505 B1 | 12/2001 | Medhkour et al. | |
| 6,394,949 B1 | 5/2002 | Crowley et al. | |
| 6,398,759 B1 | 6/2002 | Sussman et al. | |
| 6,398,775 B1 | 6/2002 | Perkins et al. | |
| 6,409,723 B1 | 6/2002 | Edwards | |
| 6,411,852 B1 | 6/2002 | Danek et al. | |
| 6,458,231 B1 | 10/2002 | Wapner et al. | |
| 6,468,313 B1 | 10/2002 | Claeson et al. | |
| D466,213 S | 11/2002 | Snitkin et al. | |
| 6,488,673 B1 | 12/2002 | Laufer et al. | |
| 6,493,589 B1 | 12/2002 | Medhkour et al. | |
| 6,508,816 B2 | 1/2003 | Shadduck | |
| 6,527,761 B1 | 3/2003 | Soltesz et al. | |
| 6,575,929 B2 | 6/2003 | Sussman et al. | |
| 6,579,270 B2 | 6/2003 | Sussman et al. | |
| 6,585,639 B1 | 7/2003 | Kotmel et al. | |
| 6,588,613 B1 | 7/2003 | Pechenik et al. | |
| 6,589,201 B1 | 7/2003 | Sussman et al. | |
| 6,592,594 B2 | 7/2003 | Rimbaugh et al. | |
| 6,599,311 B1 | 7/2003 | Biggs et al. | |
| 6,610,043 B1 | 8/2003 | Ingenito | |
| 6,629,951 B2 | 10/2003 | Laufer et al. | |
| 6,652,594 B2 | 11/2003 | Francis et al. | |
| 6,653,525 B2 | 11/2003 | Ingenito et al. | |
| 6,669,694 B2 | 12/2003 | Shadduck | |
| 6,676,628 B2 | 1/2004 | Sussman et al. | |
| 6,679,264 B1 | 1/2004 | Deem et al. | |
| 6,682,520 B2 | 1/2004 | Ingenito | |
| 6,692,494 B1 | 2/2004 | Cooper et al. | |
| 6,712,812 B2 | 3/2004 | Roschak et al. | |
| 6,719,738 B2 | 4/2004 | Mehier | |
| 6,755,794 B2 | 6/2004 | Soukup | |
| 6,770,070 B1 | 8/2004 | Balbierz | |
| 6,776,765 B2 | 8/2004 | Soukup et al. | |
| 6,860,847 B2 | 3/2005 | Alferness et al. | |
| 6,885,888 B2 | 4/2005 | Rezai | |
| 6,901,927 B2 | 6/2005 | Deem et al. | |
| 6,904,909 B2 | 6/2005 | Andreas et al. | |
| 6,907,881 B2 | 6/2005 | Suki et al. | |
| 6,911,028 B2 | 6/2005 | Shadduck | |
| 6,986,769 B2 | 1/2006 | Nelson et al. | |
| 6,997,189 B2 | 2/2006 | Biggs et al. | |
| 7,022,088 B2 | 4/2006 | Keast et al. | |
| 7,027,869 B2 | 4/2006 | Danek et al. | |
| 7,031,504 B1 | 4/2006 | Argiro et al. | |
| 7,083,612 B2 | 8/2006 | Littrup et al. | |
| 7,128,748 B2 | 10/2006 | Mooradian et al. | |
| 7,136,064 B2 | 11/2006 | Zuiderveld | |
| 7,144,402 B2 | 12/2006 | Kuester, III | |
| 7,144,588 B2 | 12/2006 | Oray et al. | |
| 7,175,644 B2 | 2/2007 | Cooper et al. | |
| 7,192,400 B2 | 3/2007 | Campbell et al. | |
| 7,198,635 B2 | 4/2007 | Danek et al. | |
| 7,233,820 B2 | 6/2007 | Gilboa | |
| 7,235,070 B2 | 6/2007 | Vanney | |
| 7,335,195 B2 | 2/2008 | Mehier | |
| 7,347,859 B2 | 3/2008 | Garabedian et al. | |
| D574,492 S | 8/2008 | Löwenstein | |
| 7,412,977 B2 | 8/2008 | Fields et al. | |
| 7,422,563 B2 | 9/2008 | Roschak et al. | |
| 7,422,584 B2 | 9/2008 | Loomas et al. | |
| 7,425,212 B1 | 9/2008 | Danek et al. | |
| D580,549 S | 11/2008 | Schwartz et al. | |
| 7,462,162 B2 | 12/2008 | Phan et al. | |
| D604,842 S | 11/2009 | Bisleri | |
| 7,628,789 B2 | 12/2009 | Soltesz et al. | |
| D610,679 S | 2/2010 | Nakagawa et al. | |
| 7,708,712 B2 | 5/2010 | Phan et al. | |
| 7,740,017 B2 | 6/2010 | Danek et al. | |
| 7,778,704 B2 | 8/2010 | Rezai | |
| 7,815,590 B2 | 10/2010 | Cooper | |
| 7,819,908 B2 | 10/2010 | Ingenito | |
| D627,066 S | 11/2010 | Romero | |
| D632,787 S | 2/2011 | Tenger et al. | |
| 7,906,124 B2 | 3/2011 | Laufer et al. | |
| 7,913,698 B2 | 3/2011 | Barry et al. | |
| D640,789 S | 6/2011 | Peine et al. | |
| D641,871 S | 7/2011 | Tenger et al. | |
| 7,985,187 B2 | 7/2011 | Wibowo et al. | |
| 7,993,323 B2 | 8/2011 | Barry et al. | |

(56) References Cited

U.S. PATENT DOCUMENTS

| | | | |
|---|---|---|---|
| 8,002,740 B2 | 8/2011 | Willink et al. | |
| D646,384 S | 10/2011 | Gauthier et al. | |
| D646,385 S | 10/2011 | Gauthier et al. | |
| D650,073 S | 12/2011 | Pedersen et al. | |
| D652,920 S | 1/2012 | Sherwood et al. | |
| 8,088,127 B2 | 1/2012 | Mayse et al. | |
| 8,172,827 B2 | 5/2012 | Deem et al. | |
| 8,187,269 B2 | 5/2012 | Shadduck et al. | |
| 8,251,070 B2 | 8/2012 | Danek et al. | |
| 8,292,882 B2 | 10/2012 | Danek et al. | |
| 8,322,335 B2 | 12/2012 | Barry et al. | |
| 8,568,141 B2 | 10/2013 | Tanaka et al. | |
| 8,585,645 B2 | 11/2013 | Barry et al. | |
| 8,626,495 B2 | 1/2014 | Boldt et al. | |
| 8,628,495 B2 * | 1/2014 | Horton | A61M 5/1452 604/151 |
| 8,734,380 B2 | 5/2014 | Barry et al. | |
| 8,858,549 B2 | 10/2014 | Shadduck et al. | |
| D717,431 S | 11/2014 | Cardinale et al. | |
| 8,900,223 B2 | 12/2014 | Shadduck | |
| 9,050,076 B2 | 6/2015 | Barry et al. | |
| 9,113,858 B2 | 8/2015 | Barry et al. | |
| D774,034 S | 12/2016 | Kheradpir et al. | |
| D776,874 S | 1/2017 | Kling et al. | |
| D777,321 S | 1/2017 | Nakagami et al. | |
| D777,914 S | 1/2017 | Wapler et al. | |
| 9,561,068 B2 | 2/2017 | Sharma et al. | |
| D785,185 S | 4/2017 | Yang et al. | |
| D812,744 S | 3/2018 | Robinson et al. | |
| D813,400 S | 3/2018 | Bechtel et al. | |
| 2002/0077516 A1 | 6/2002 | Flanigan | |
| 2002/0111386 A1 | 8/2002 | Sekins et al. | |
| 2002/0112723 A1 | 8/2002 | Schuster et al. | |
| 2002/0177846 A1 | 11/2002 | Mulier et al. | |
| 2003/0099279 A1 | 5/2003 | Venkatasubramanian et al. | |
| 2003/0130650 A1 | 7/2003 | Yaron | |
| 2003/0181917 A1 * | 9/2003 | Gertner | A61M 35/003 606/82 |
| 2003/0181922 A1 | 9/2003 | Alferness | |
| 2004/0031494 A1 | 2/2004 | Danek et al. | |
| 2004/0038868 A1 | 2/2004 | Ingenito | |
| 2004/0047855 A1 | 3/2004 | Ingenito | |
| 2004/0055606 A1 | 3/2004 | Hendricksen et al. | |
| 2004/0068306 A1 | 4/2004 | Shadduck | |
| 2004/0199226 A1 | 10/2004 | Shadduck | |
| 2004/0200484 A1 | 10/2004 | Springmeyer | |
| 2004/0244803 A1 | 12/2004 | Tanaka | |
| 2005/0016530 A1 | 1/2005 | McCutcheon et al. | |
| 2005/0066974 A1 | 3/2005 | Fields et al. | |
| 2005/0166925 A1 | 8/2005 | Wilson et al. | |
| 2005/0171396 A1 | 8/2005 | Pankratov et al. | |
| 2005/0171582 A1 | 8/2005 | Matlock | |
| 2005/0203483 A1 | 9/2005 | Perkins et al. | |
| 2005/0215991 A1 | 9/2005 | Altman et al. | |
| 2005/0222485 A1 | 10/2005 | Shaw et al. | |
| 2006/0004400 A1 | 1/2006 | McGurk et al. | |
| 2006/0047291 A1 | 3/2006 | Barry | |
| 2006/0100619 A1 | 5/2006 | McClurken et al. | |
| 2006/0130830 A1 | 6/2006 | Barry | |
| 2006/0135955 A1 | 6/2006 | Shadduck | |
| 2006/0162731 A1 | 7/2006 | Wondka et al. | |
| 2006/0200076 A1 | 9/2006 | Gonzalez et al. | |
| 2006/0224154 A1 * | 10/2006 | Shadduck | A61B 18/04 606/41 |
| 2007/0032785 A1 | 2/2007 | Diederich et al. | |
| 2007/0036417 A1 | 2/2007 | Argiro et al. | |
| 2007/0068530 A1 | 3/2007 | Pacey | |
| 2007/0091087 A1 | 4/2007 | Zuiderveld | |
| 2007/0092864 A1 | 4/2007 | Reinhardt et al. | |
| 2007/0102011 A1 | 5/2007 | Danek et al. | |
| 2007/0106292 A1 | 5/2007 | Kaplan et al. | |
| 2007/0109299 A1 | 5/2007 | Peterson | |
| 2007/0112349 A1 | 5/2007 | Danek et al. | |
| 2007/0118184 A1 | 5/2007 | Danek et al. | |
| 2007/0137646 A1 | 6/2007 | Weinstein et al. | |
| 2007/0293853 A1 | 12/2007 | Truckai et al. | |
| 2008/0033493 A1 | 2/2008 | Deckman et al. | |
| 2008/0132826 A1 | 6/2008 | Shadduck et al. | |
| 2008/0281267 A1 * | 11/2008 | Mehier | A61B 18/04 604/113 |
| 2009/0018538 A1 | 1/2009 | Webster et al. | |
| 2009/0043301 A1 | 2/2009 | Jarrard et al. | |
| 2009/0138001 A1 | 5/2009 | Barry et al. | |
| 2009/0149846 A1 | 6/2009 | Hoey et al. | |
| 2009/0192508 A1 | 7/2009 | Laufer et al. | |
| 2009/0216220 A1 | 8/2009 | Hoey et al. | |
| 2009/0306640 A1 * | 12/2009 | Glaze | A61B 17/12045 606/27 |
| 2009/0312753 A1 | 12/2009 | Shadduck et al. | |
| 2010/0094270 A1 | 4/2010 | Sharma | |
| 2010/0204688 A1 | 8/2010 | Hoey et al. | |
| 2010/0256714 A1 | 10/2010 | Springmeyer | |
| 2010/0262133 A1 | 10/2010 | Hoey et al. | |
| 2011/0077628 A1 | 3/2011 | Hoey et al. | |
| 2011/0160648 A1 | 6/2011 | Hoey | |
| 2011/0270031 A1 | 11/2011 | Frazier et al. | |
| 2011/0301587 A1 | 12/2011 | Deem et al. | |
| 2012/0016363 A1 | 1/2012 | Mayse et al. | |
| 2012/0016364 A1 | 1/2012 | Mayse et al. | |
| 2013/0006231 A1 | 1/2013 | Sharma et al. | |
| 2013/0267939 A1 | 10/2013 | Barry et al. | |
| 2014/0324037 A1 | 10/2014 | Hoey et al. | |
| 2015/0094607 A1 | 4/2015 | Barry et al. | |
| 2015/0230852 A1 | 8/2015 | Barry et al. | |
| 2016/0151103 A1 | 6/2016 | Henne et al. | |
| 2016/0220297 A1 | 8/2016 | Kroon et al. | |
| 2017/0164999 A1 | 6/2017 | Hettel | |
| 2017/0231676 A1 | 8/2017 | Sharma et al. | |

FOREIGN PATENT DOCUMENTS

| | | |
|---|---|---|
| EP | 1143864 B1 | 2/2004 |
| EP | 1173103 B1 | 10/2005 |
| EP | 1326549 B1 | 12/2005 |
| EP | 1326548 B1 | 1/2006 |
| EP | 1485033 B1 | 8/2009 |
| EP | 1485033 B1 | 8/2009 |
| WO | 0011927 A2 | 3/2000 |
| WO | WO 00/11927 A2 | 3/2000 |
| WO | 0102042 A1 | 1/2001 |
| WO | WO 01/02042 A1 | 1/2001 |
| WO | 02069821 A1 | 9/2002 |
| WO | WO 02/069821 A1 | 9/2002 |
| WO | 03028540 A2 | 4/2003 |
| WO | 03070302 A1 | 8/2003 |
| WO | WO 03/070302 A1 | 8/2003 |
| WO | 03086498 A2 | 10/2003 |
| WO | WO 03/086498 A2 | 10/2003 |
| WO | 2005025635 A2 | 3/2005 |
| WO | WO 2005/025635 A2 | 3/2005 |
| WO | 2005102175 A2 | 11/2005 |
| WO | WO 2005/102175 A2 | 11/2005 |
| WO | 2006003665 A2 | 1/2006 |
| WO | WO 2006/003665 A2 | 1/2006 |
| WO | 2006052940 A2 | 5/2006 |
| WO | 2006053308 A2 | 5/2006 |
| WO | 2006053309 A2 | 5/2006 |
| WO | WO 2006/052940 A2 | 5/2006 |
| WO | WO 2006/053308 A2 | 5/2006 |
| WO | WO 2006/053309 A2 | 5/2006 |
| WO | 2006080015 A2 | 8/2006 |
| WO | WO 2006/080015 A2 | 8/2006 |
| WO | 2006116198 A2 | 11/2006 |
| WO | WO 2006/116198 A2 | 11/2006 |
| WO | 2008051706 A2 | 5/2008 |
| WO | WO 2008/051706 A2 | 5/2008 |
| WO | 2009009236 A1 | 1/2009 |
| WO | 2009009398 A1 | 1/2009 |
| WO | 2009015278 A1 | 1/2009 |
| WO | WO 2009/009236 A1 | 1/2009 |
| WO | WO 2009/009398 A1 | 1/2009 |
| WO | WO 2009/015278 A1 | 1/2009 |
| WO | 2009137819 A1 | 11/2009 |
| WO | WO 2009/137819 A1 | 11/2009 |

(56) References Cited

FOREIGN PATENT DOCUMENTS

| WO | 2010042461 A1 | 4/2010 |
|---|---|---|
| WO | WO 2010/042461 A1 | 4/2010 |
| WO | 2011006020 A1 | 1/2011 |
| WO | 2011056684 A2 | 5/2011 |
| WO | 2011060201 A1 | 5/2011 |
| WO | WO 2011/056684 A2 | 5/2011 |
| WO | WO 2011/060200 A1 | 5/2011 |
| WO | WO 2011/060201 A1 | 5/2011 |
| WO | 2011127216 A2 | 10/2011 |
| WO | WO 2011/127216 A2 | 10/2011 |

OTHER PUBLICATIONS

Blacker, G. F.; Vaporization of the uterus; J. of Obstetrics and Gynaecology; vol. 33; pp. 488-511; (year of publication is sufficiently earlier than the effective U.S. filing date and any foreign priority date) 1902.

Carpenter III et al.; Comparison of endoscopic cryosurgery and electrocoagulation of bronchi; Trans. Amer. Acad. Opth.; vol. 84; No. 1; pp. ORL-313-ORL-323; Jan. 1977.

Clinical Trials.Gov.; Study of the AeriSeal System for HyPerinflation Reduction in Emphysema; 4 pages; Nov. 5, 2014; retrieved from the internet (http://clinicaltrials.gov/show/NCT01449292).

Coda, et al., "Effects of pulmonary reventilation on gas exchange after cryolytic disobstruction of endobronchial tumors," Minerva Medical, vol. 72, pp. 1627-1631, Jun. 1981 (w/ Eng. Trans.).

Delaunois; Anatomy and physiology of collateral respiratory pathways; Eur. Respir. J.; 2(9); pp. 893-904; Oct. 1989.

Eyal et al.; The acute effect of pulmonary burns on lung mechanics and gas exchange in the rabbit; Br. J. Anaesth.; vol. 47; pp. 546-552; (year of publication is sufficiently earlier than the effective U.S. filing date and any foreign priority date) 1975.

Ferlay et al.; GLOBOCAN 2008 v1.2, Cancer Incidence and Mortality Worldwide: IARC CancerBase No. 10 [internet]; 16 pages; retrieved from the internet (http://www.iarc.fr/en/media-centre/iarcnews/2010/GLOBOCAN2008.pdf); Lyon, France: International Agency for Research on Cancer; Jun. 1, 2010.

Fishman et al., A randomized trial comparing lung-volume-reduction surgery with medical therapy for severe emphysema, N Engl J Med, vol. 348, No. 21, pp. 2059-2073, May 22, 2003.

Goldberg et al.; Radiofrequency tissue ablation in the rabbit lung: Efficacy and complications; Acad. Radiol.; vol. 2; pp. 776-784; Sep. 1995.

Herth et al.; Efficacy predictors of lung volume reduction with zephyr valves in a european cohort; Eur. Respir. J.; 39(6); pp. 1334-1342; Jun. 2012.

Homasson, et al., "Bronchoscopic cryotherapy for airway strictures caused by tumors," Chest, vol. 90, No. 2, pp. 159-164, Aug. 1986.

Kang, Li, "Efficient optimal net surface detection for image segmentation—from theory to practice," M.Sc. Thesis, The University of Iowa, Dec. 2003.

Kinsella et al.; Quantitation of emphysema by computed tomography using a "densitymask" program and correlation with pulmonary function tests; Chest; 97(2); pp. 315-321; Feb. 1990.

Looga, R. U.; Mechanism of changes in the respiratory and cardiovascular reflexes from the lungs associated with intrapulmonary steam burns; Eng. Trans. from Byulleten Eksperimental noi Biologii I Meditsiny; vol. 61; No. 6; pp. 31-33; Jun. 1966.

Marasso, et al., "Cryosurgery in bronchoscopic treatment of tracheobronchial stenosis," Chest, vol. 103, No. 2, pp. 472-474, Feb. 1993.

Marasso, et al., "Radiofrequency resection of bronchial tumours in combination with cryotherapy: evaluation of a new technique," Thorax, vol. 53, pp. 106-109, (year of publication is sufficiently earlier than the effective U.S. filing date and any foreign priority date) 1998.

Mathur et al., Fiberoptic bronchoscopic cryotherapy in the management of tracheobronchial obstruction, Chest, vol. 110, No. 3, pp. 718-723, Sep. 1996.

Morice et al.; Endobrinchial argon plasma coagulation for treatment of hemotysis and neoplastic airway obstruction, Chest, vol. 119, No. 3, pp. 781-787, Mar. 2001.

Moritz et al.; The effects of inhaled heat on the air pasage and lungs; American Journal of Pathology; vol. XXI; pp. 311-331; (year of publication is sufficiently earlier than the effective U.S. filing date and any foreign priority date) 1944.

Moulding et al.; Preliminary studies for achieving transcervical oviduct occlusion by hot water or low-pressure steam; Advances in Planned Parenthood; vol. 12, No. 2; pp. 79-85; (year of publication is sufficiently earlier than the effective U.S. filing date and any foreign priority date) 1977.

National Lung Screening Trial Research Team; Reduced lung-cancer mortality with low-close computed tomographic screening; N. Eng. J. Med.; 365(5); pp. 395-409; Aug. 4, 2011.

Pracht, Adam, "VIDA takes new approach," Iowa City Press-Citizen, Sep. 12, 2005.

Quin, Jacquelyn, "Use of neodymium yttrium aluminum garnet laser in long-term palliation of airway obstruction," Connecticut Medicine, vol. 59, No. 7, pp. 407-412, Jul. 1995.

Sciurba et al.; A randomized study of endobronchial valves for advanced emphysema; N. Eng. J. Med.; 363(13); pp. 1233-1244; Sep. 23, 2010.

Shah et al.; Collateral ventilation and selection of techniques for bronchoscopic lung volume reduction; Thorax; 67(4); pp. 285-286; Apr. 2012.

Slebos et al.; Bronchoscopic lung volume reduction coil treatment of patients with severe heterogeneous emphysema; Chest; 142(3); pp. 574-582; Sep. 2012.

Sutedja, et al.; Bronchoscopic treatment of lung tumors; Elsevier, Lung Cancer, 11, pp. 1-17, Jul. 1994.

Tschirren et al.; Intrathoracic airway trees: segmentation and airway morphology analysis from low-dose CT scans; IEEE Trans. Med. Imaging; vol. 24, No. 12; pp. 1529-1539; Dec. 2005.

Tschirren, Juerg; Segmentation, anatomical labeling, branchpoint matching, and quantitative analysis of human airway trees in volumetric CT images; Ph.D. Thesis; The University of Iowa; Aug. 2003.

Tschirren, Juerg; Segmentation, anatomical labeling, branchpoint matching, and quantitative analysis of human airway trees in volumetric CT images; Slides from Ph.D. defense; The University of Iowa; Jul. 10, 2003.

Van De Velde; Vapo-cauterization of the uterus; Amer. J. Med. Sci.; vol. CXVIII; (year of publication is sufficiently earlier than the effective U.S. filing date and any foreign priority date) 1899.

Vorre et al.; Morphology of tracheal scar after resection with CO2-laser and high-frequency cutting loop; Acta Otolaryngol (Stockh); vol. 107; pp. 307-312; (year of publication is sufficiently earlier than the effective U.S. filing date and any foreign priority date) 1989.

Henne et al.; U.S. Appl. No. 14/957,433 entitled "Vapor treatment of lung nodules and tumors," filed Dec. 2, 2015.

PCT/US2018/063167 ISR and Opinion dated Feb. 8, 2019.

Van De Velde, "Vapo-cauterization of the uterus," Amer.J.Med, Sci vol. CXVII, 1899.

Vorre, et al., "Morphology of tracheal scar after resection with C02 laser and high-frequency cutting loop," Acta Otolaryngol (Stockh), vol. 107, 1989.

\* cited by examiner

MEDICAL VAPOR GENERATOR

CROSS REFERENCE TO RELATED APPLICATIONS

This application claims the benefit under 35 U.S.C. § 119 of U.S. Provisional Application No. 62/111,033, titled "Medical Vapor Generator", filed Feb. 2, 2015, and U.S. Provisional Application No. 62/153,352, titled "Medical Vapor Generator", filed Apr. 27, 2015, the disclosures of which are both incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Condensable vapor, such as water vapor, has been used to perform a variety of medical procedures. For example, U.S. Pat. No. 7,993,323 describes a medical vapor generator system that generates and delivers condensable vapor to perform lung volume reduction as an emphysema therapy. Other early medical vapor generators are described in US 2002/0177846 and US 2009/0216220. These publications describe therapeutic methods including treating, e.g., the liver, breast, gall bladder, stomach, pancreas, colon, urinary bladder, prostate, bone, vertebrae, eye and brain.

SUMMARY OF THE DISCLOSURE

A medical vapor system comprising a fluid conduit having an inlet, an outlet and a heating section, the inlet being adapted and configured to be connected to a source of liquid water; a resistance heater disposed and configured to generate heat and conduct the heat to the heating section of the fluid conduit to vaporize liquid water flowing through the heating section, a power supply operatively connected to the heater, and a controller adapted to control production of water vapor by the system.

In some embodiments, the heating section of the fluid conduit is coiled around at least part of the resistance heater. In one embodiment, the heating section of the fluid conduit is coiled within at least part of the resistance heater. In another embodiment, the system further comprises a housing enclosing the heating section of the fluid conduit and the heater.

In some embodiments, the housing is a handheld housing comprising a handle.

In one embodiment, the system further comprises a vapor delivery member adapted to receive vapor from the fluid conduit outlet. In another embodiment, the vapor delivery member comprises a vapor delivery catheter.

In some embodiments, the controller is further adapted to control electrical current flowing to the heater.

In one embodiment, the system comprises a temperature sensor adapted to send a signal to the controller corresponding to a temperature of water vapor within the conduit or at the conduit outlet.

In another embodiment, the system comprises a valve communicating with the controller to control water flow through the fluid conduit. In some embodiments, the system comprises a valve communicating with the controller to control steam flow through the outlet.

A medical vapor system is provided, comprising a fluid conduit having an inlet, an outlet and a heating section, the inlet being adapted and configured to be connected to a source of liquid water, the heating section being formed of a conductive material, a power supply operatively connected to the heating section to apply a voltage across the heating section to generate resistive heat to the heating section to vaporize liquid water flowing through the heating section, and a controller adapted to control production of water vapor by the system.

In some embodiments, the heating section is a helix.

In one embodiment, the system further comprises a housing enclosing the heating section of the fluid conduit and the heater. In some embodiments, the housing is a handheld housing comprising a handle.

In one embodiment, the system further comprises a vapor delivery member adapted to receive vapor from the fluid conduit outlet. In some embodiments, the vapor delivery member comprises a vapor delivery catheter.

In one embodiment, the controller is further adapted to control electrical current flowing to the heating section.

In another embodiment, the system further comprises a syringe and a stepper motor operably connected to a plunger within the syringe, the syringe comprising an outlet in fluid communication with the fluid conduit. In some embodiments, the syringe further comprises an inlet communicable with a water source and an inlet check valve arranged to permit fluid to enter the syringe through the inlet and to prevent fluid from exiting the syringe through the inlet. In further embodiments, the syringe further comprises an outlet check valve arranged to permit fluid to exit the syringe through the outlet and to prevent fluid from entering the syringe through the outlet.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Because the primary heat delivery mechanism of condensable vapor is the heat released to tissue when the vapor condenses to liquid, it is important to control the quality of the vapor as well as the vapor flow rate. It may also be important to reduce the cost and complexity of medical vapor generators by, e.g., avoiding the use of expensive capital equipment, such as RF generators. Finally, for applications requiring the delivery of condensable vapor to locations within a patient's body, it may be desirable to generate the vapor close to the portion of the vapor delivery lumen entering the body so as to minimize heat loss and possible condensation before the vapor reaches the target tissue.

Prior publications have described the use of resistance heaters to vaporize standing water within a vessel and to deliver the water vapor through a conduit or instrument to the target patient tissue. Prior publications have also described the use of RF energy to vaporize water flowing through a conduit within a vapor delivery tool. The prior art has not described the use of an inexpensive resistance heater to vaporize water flowing through a vapor delivery tool. More specifically, the prior art has not disclosed a self-contained portable disposable vapor delivery device containing a fluid flow controller (e.g., a pump or pressurized fluid source), a heating element (e.g., a resistive heater), a vapor generation element (e.g., a lumen or reservoir in which the liquid to vapor phase change occurs), a power supply, and a controller (to, e.g., monitor vapor parameters and to control heating and fluid flow).

Figure 1:
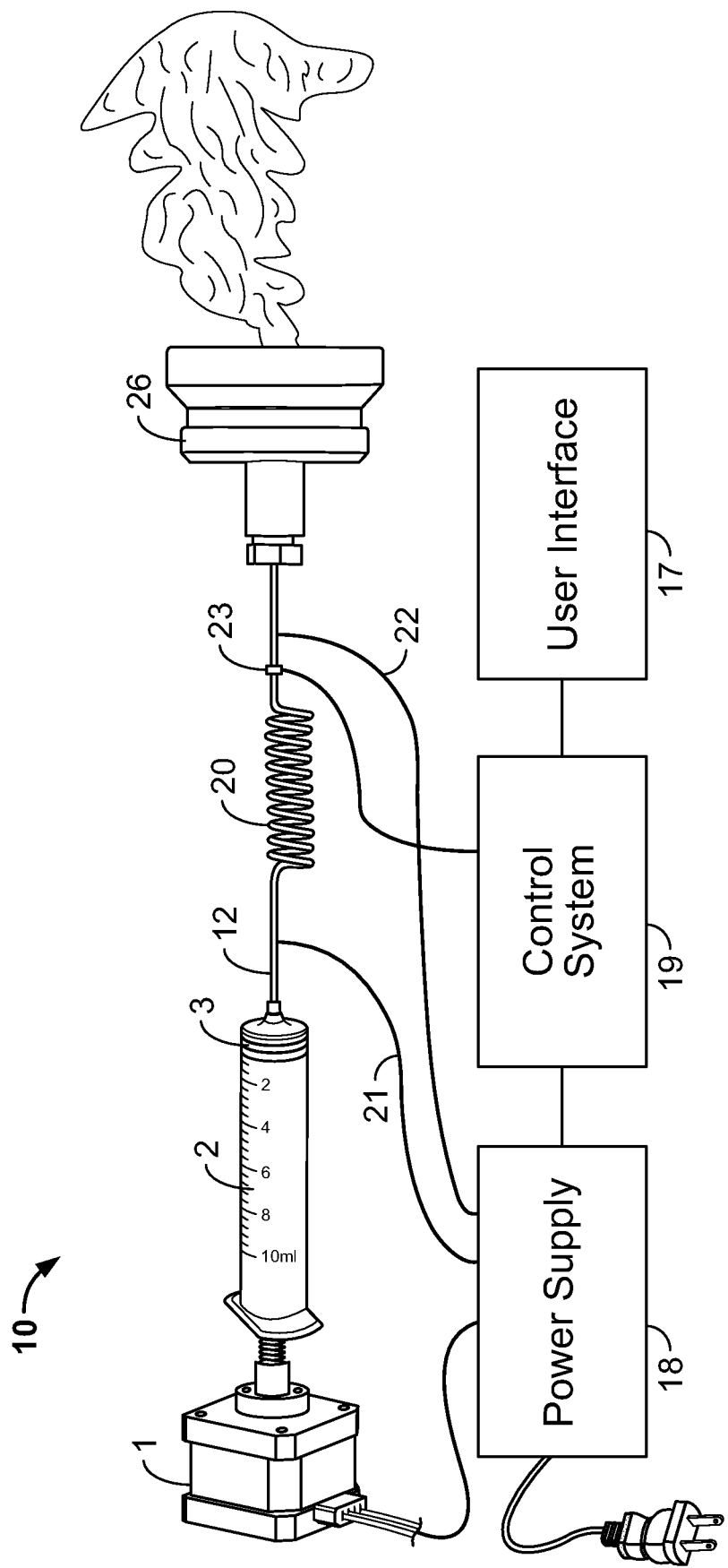
FIG. 1 shows an embodiment of the medical vapor generator of this invention.

FIG. 1 shows an embodiment of the invention. Medical vapor generator 10 has a fluid conduit 12 receiving liquid water from a water source. In this embodiment, the water source is a stepper motor 1 that advances the piston or plunger 3 of a syringe 2. Motor 1 is powered and controlled by power supply 18 under the control of control system 19. In some embodiments, power supply 18 is an electrically isolated power supply, such as one or more rechargeable batteries. A user interface 17 enables a user to input vapor delivery parameters and provides output to the user.

In this embodiment, fluid conduit 12 is a conduit formed of a conductive material, such as a metal hypotube, with a heating portion 20 optionally formed in a helix. Leads 21 and 22 connect direct current from power supply 18 to the heating section 20 to resistively heat the heating section 20 and any water flowing through it from the syringe 2. In alternative embodiments, an alternating current source may be used. Water flowing through the heating section 20 of conduit 12 is vaporized before entering a vapor delivery member (not shown) connected to connector 26. One or more temperature sensors, such as thermocouple 23 at the outlet of the heating section 20, may be used by the control system 19 to obtain information about the temperature of the vapor in order to, e.g., regulate power delivery, maintain a baseline temperature and/or detect and mitigate system failure.

Figure 2:
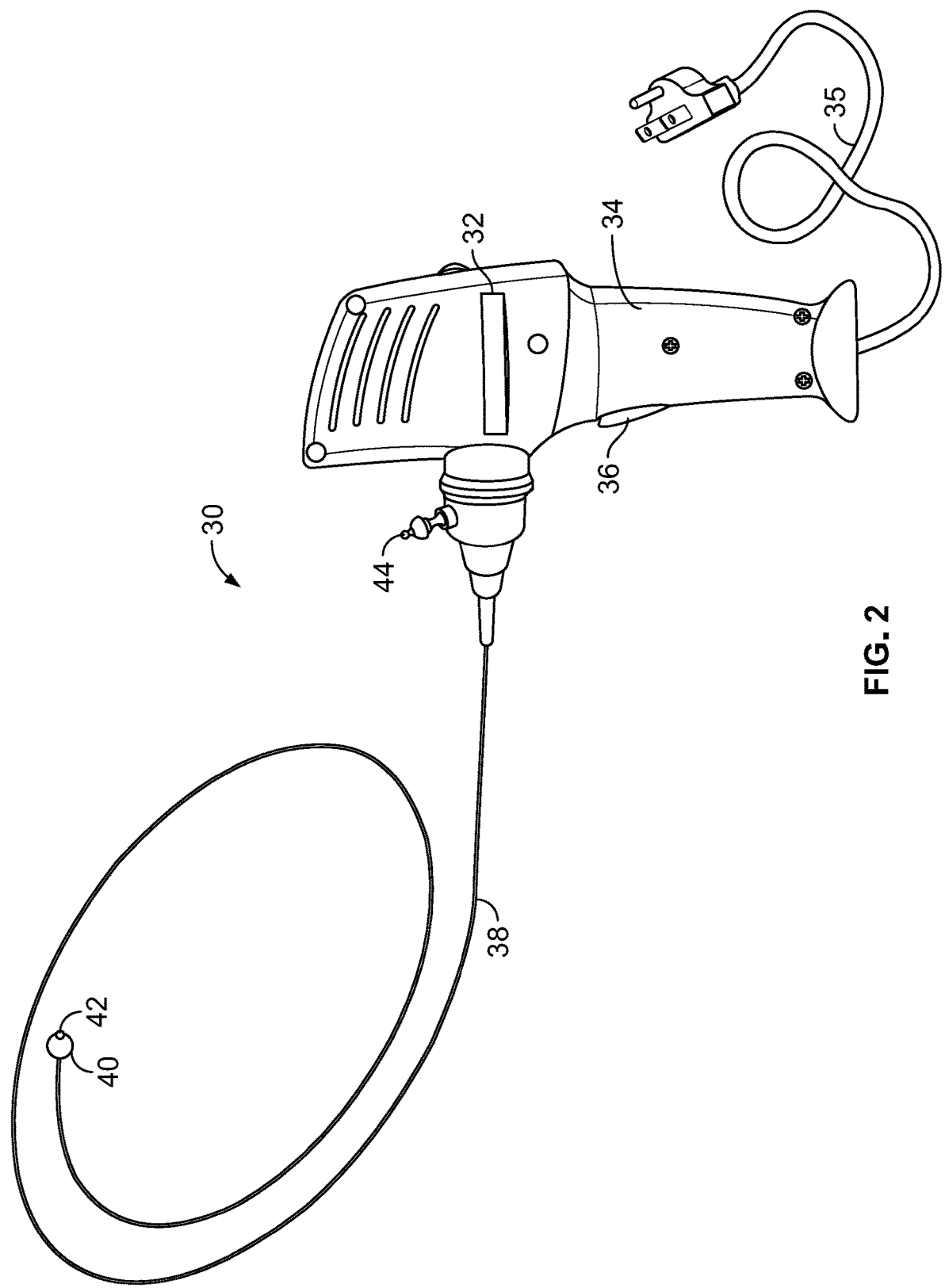
FIG. 2 shows another embodiment of the medical vapor generator of this invention.

FIG. 2 shows another embodiment of a medical vapor system 30 according to this invention. In this embodiment, the fluid conduit, the coiled resistance heater and controller are all housed within a single housing 32 having a handle 34 and user input control 36. In some embodiments, depressing input control 36 starts water vapor generation and delivery, and releasing user input control 36 ceases water vapor generation and delivery.

Water vapor generated within housing 32 exits into a vapor delivery member. In this embodiment, the vapor delivery member is a removable catheter 38 with an inflatable balloon 40 disposed proximal to the distal exit port 42 of the catheter. Balloon 40 may be inflated using, e.g., a syringe connected at port 44. The resistance heater may be structured as described above with respect to FIG. 1. Other vapor delivery tools may be used connected to the vapor generator of this invention, such as a needle, a double balloon (i.e., a catheter with a balloon proximal and distal to the catheter outlet, or a balloon just distal to the catheter outlet), etc. Power may be supplied via a power cord 35 (connecting to, e.g., wall current) or by a battery disposed within housing 32. In addition, the power supply element can be removed from the housing in order to reduce cost of the disposable component of the invention, and/or to allow recharging if said power supply is a rechargeable battery. A GUI or other user interface may also be provided in or on housing 32 to receive user inputs (e.g., to control power, vapor flow and/or vapor delivery time) and to display information about the generator and its use. The user inputs can be provided via buttons, touch screen, etc. In some embodiments, the output parameters of the vapor generator (e.g., vapor delivery time, vapor flow rate, etc.) can be preprogrammed so that each unit has a specific set of operating parameters.

Figure 3A:
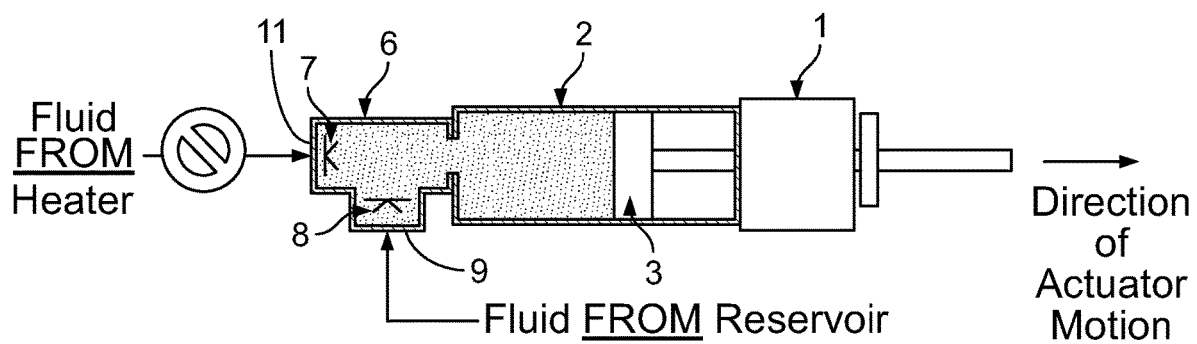
FIGS. 3A and 3B show filling and delivery operations for a medical vapor generator of this invention.
Figure 3B:
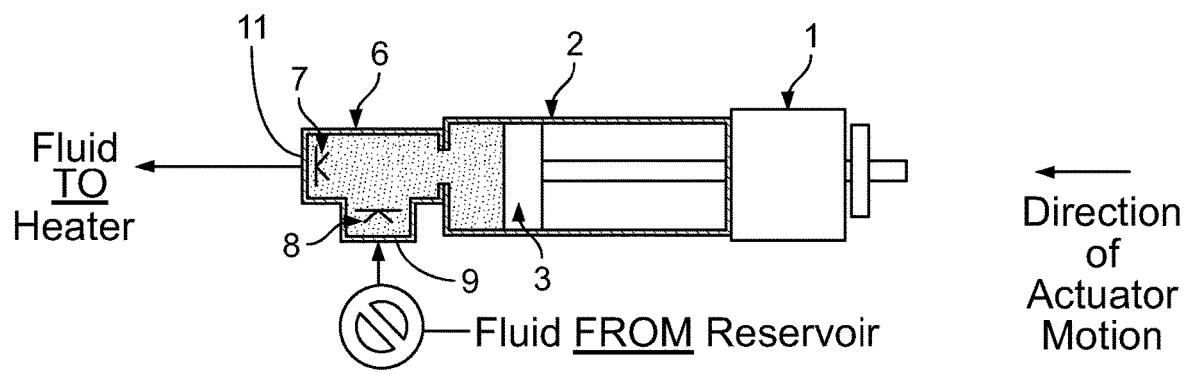

FIGS. 3A and 3B illustrate a syringe valve arrangement useful for filling the syringe with water and delivering water to the heater. In FIG. 3A, the stepper motor 1 moves the syringe plunger 3 away from the syringe inlet 9. An inlet check valve 8 permits water to be drawn into syringe 2 from a water source (not shown), and an outlet check valve 7 keeps syringe outlet 11 closed. In FIG. 3B, the direction of the stepper motor is reversed. As plunger 3 moves toward syringe outlet 11, check valve 8 closes and check valve 7 opens, enabling water to be expelled from syringe outlet 11 into the conduit leading to the device's water heating section.

An advantage of the medical vapor generator described above is the relatively low heat capacity of the resistive heater section. This provides for the rapid start, and the rapid cessation, of vapor delivery.

These embodiments of the invention provide a medical vapor delivery device containing a fluid flow controller (such as, e.g., the syringe and stepper motor described above), a vapor generation element (e.g., a resistively heated coiled section of the fluid conduit), a power supply, a controller and a user interface that is portable, self-contained and disposable.

In some embodiments, the water entering the heating section of the fluid conduit may be preheated in a reservoir upstream of the heating section. Some of the water may also be vaporized prior to entering the heating section of the conduit, with the resistance heater providing added energy to the flowing vapor (or mixture of vapor and liquid) to maintain the quality of the steam by replenishing the heating section at a rate similar to the delivery rate so as to minimize temperature loss in the heating section during vapor delivery. The system may be provided with a dielectric strength exceeding 4 kV to meet medical device safety standards. A valve at the vapor outlet would also enable vapor delivery to cease on demand or in response to a signal from the controller even if vapor production has not yet ceased.

The baseline condition of the heating element prior to therapy may affect subsequent vapor delivery during therapy. Controlling the temperature and water content before treatment may therefore improve consistency of the vapor treatment. Thus, in some embodiments, energy and/or water may be applied to the heating element to maintain its baseline condition before treatment. In one embodiment, the device is operated in an idle mode in which energy and water are supplied to the heating element at a constant, slow rate to maintain its temperature and water content. Vapor may be generated, but the vapor may condense prior to reaching the outlet of the delivery member. In another embodiment, the idle mode provides a dry idle; energy is applied to heat the heating element (to, e.g., 98° C., with possible feedback control via a thermocouple or other temperature sensor to prevent overheating), but no water is supplied to the heating element. In yet another embodiment, a pre-idle stage is added to the beginning of a therapy session, during which energy and water are supplied for a short period of time, such as 5 seconds, directly before treatment.

The device's water source (e.g., syringe 2 in FIG. 1) may be prefilled prior to shipping to the ultimate user. Alternatively, the water source (such as syringe 2 of FIG. 1) may be filled manually (e.g., using another medical syringe) or automatically (using the stepper motor, such as described with respect to FIGS. 3A and 3B) just prior to use. In some embodiments, the system's power supply and controller may be disposed in a first housing and the system's water source, heater and motor or other pump may be disposed in a second housing.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention.

What is claimed is:

1. A medical vapor system comprising:
   a portable hand-held housing;
   a discrete fluid conduit having an inlet, an outlet and a heating section all of which are self-contained within said portable hand-held housing, the inlet being adapted and configured to receive liquid water from a source of liquid water; and the heating section being adapted to vaporize liquid water into water vapor flowing through the heating section based on resistive heating when a voltage difference is applied across the heating section of the fluid conduit, and said outlet being adapted and configured to be connected to a removable vapor delivery member, said removable vapor delivery member adapted to receive water vapor from said outlet;
   a power supply operatively connected to apply a voltage difference from a first location of the heating section of the fluid conduit and to a second location of the heating section, thereby avoiding conduction of an electrical current and resistive heat generation outside of the heating section; and
   a controller adapted to control production of water vapor by the medical vapor system.

2. The system of claim 1 wherein the heating section of the fluid conduit is helix-shaped.

3. The system of claim 1 wherein the portable hand-held housing further comprises a user input control.

4. The system of claim 3 wherein the user input control on the portable hand-held housing is adapted to start and stop the water vapor generation and delivery.

5. The system of claim 1 wherein said removable vapor delivery member comprises a vapor delivery catheter.

6. The system of claim 1 wherein the controller is further adapted to control electrical current flowing to the heating section.

7. The system of claim 1 further comprising a temperature sensor adapted to send a signal to the controller corresponding to a temperature of the water vapor within the discrete fluid conduit or at the conduit outlet.

8. The system of claim 1 further comprising a valve communicating with the controller to control the liquid water flow through the discrete fluid conduit.

9. The system of claim 1 further comprising a valve communicating with the controller to control the water vapor flow through the outlet.

10. A medical vapor system comprising:
    a fluid conduit having an inlet, an outlet and a heating section, the inlet being adapted and configured to transport a flow of liquid water to the heating section, and the heating section being a lengthwise portion of the fluid conduit and formed of an electrically conductive material;
    a first lead connected to a proximal section of the heating section, and a second lead connected to a distal region of the heating section;
    a power supply operatively connected to the heating section via the first lead and second lead to apply a voltage across the heating section to generate resistive heat along the heating section of the fluid conduit to vaporize the flow of liquid water flowing therethrough into water vapor; and
    a controller adapted to control production of said water vapor by the medical vapor system.

11. The system of claim 10 wherein the heating section is a helix.

12. The system of claim 10 wherein the system further comprises a housing enclosing the heating section of the fluid conduit.

13. The system of claim 12 wherein the housing is a handheld housing comprising a handle.

14. The system of claim 10 further comprising a vapor delivery member adapted to receive vapor from the fluid conduit outlet.

15. The system of claim 14 wherein the vapor delivery member comprises a vapor delivery catheter.

16. The system of claim 10 wherein the controller is further adapted to control electrical current flowing to the heating section.

17. The system of claim 10 further comprising a syringe and a stepper motor operably connected to a plunger within the syringe, the syringe comprising an outlet in fluid communication with the fluid conduit.

18. The system of claim 17 wherein the syringe further comprises an inlet communicable with a water source and an inlet check valve arranged to permit fluid to enter the syringe through the inlet and to prevent fluid from exiting the syringe through the inlet.

19. The system of claim 18 wherein the syringe further comprises an outlet check valve arranged to permit fluid to exit the syringe through the outlet and to prevent fluid from entering the syringe through the outlet.

20. The system of claim 2 wherein the fluid conduit is a metal hypotube.

\* \* \* \* \*